US012746361B2

(12) United States Patent
Schultz

(10) Patent No.: US 12,746,361 B2
(45) **Date of Patent: *Sep. 29, 2026**

(54) VENTILATOR CONDENSATION TRAP

(71) Applicant: Joseph P. Schultz, Atlanta, GA (US)

(72) Inventor: Joseph P. Schultz, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,602

(22) Filed: Dec. 6, 2023

(65) Prior Publication Data

US 2024/0100285 A1 Mar. 28, 2024

Related U.S. Application Data

(63) Continuation of application No. 17/092,287, filed on Nov. 8, 2020, now Pat. No. 11,857,728.

(60) Provisional application No. 62/932,920, filed on Nov. 8, 2019.

(51) Int. Cl.
*A61M 16/08* (2006.01)
*A61M 16/10* (2006.01)
*A61M 16/16* (2006.01)
*A61M 16/20* (2006.01)

(52) U.S. Cl.
CPC .... *A61M 16/0808* (2013.01); *A61M 16/0816* (2013.01); *A61M 16/0875* (2013.01); *A61M 16/1045* (2013.01); *A61M 16/20* (2013.01); *A61M 16/16* (2013.01)

(58) Field of Classification Search
CPC .............. A61M 16/00; A61M 16/0054; A61M 16/0057; A61M 16/01; A61M 16/08; A61M 16/0808; A61M 16/0816; A61M 16/0875; A61M 16/0883; A61M 16/0891; A61M 16/1045; A61M 16/105; A61M 16/106; A61M 16/1065; A61M 16/107; A61M 16/16
See application file for complete search history.

(56) References Cited

U.S. PATENT DOCUMENTS 4,333,451 A * 6/1982 Paluch .............. A61M 16/0808 128/911
5,228,436 A * 7/1993 Parkin ............... A61M 16/0833 128/205.12
6,523,538 B1 * 2/2003 Wikefeldt ......... A61M 16/0808 128/205.12
7,802,574 B2 9/2010 Schultz
(Continued)

OTHER PUBLICATIONS

Perma Prure, “All About Nafion”, https://web.archive.org/web/20180523122802/http://www.permapure.com/resources/all-about-nafion-and-faq; retrieved with date May 23, 2018.*

*Primary Examiner* — Joseph D. Boecker
(74) *Attorney, Agent, or Firm* — Merchant & Gould P.C.

(57) ABSTRACT

Condensation traps are disclosed herein for the purpose of trapping and removing water condensed from the humidified air present within respiratory ventilatory systems and tubing. Traps disclosed herein can be positioned inline with the tubing, and therefore allow the trap to be positioned very near the patient interface, and minimize dead space between the trap and the patient interface. Minimizing the dead space in this manner prevents water from condensing prior to entering the trap. Respiratory ventilator systems incorporating condensation traps and methods of mechanical ventilation relying on condensation traps are also disclosed herein.

18 Claims, 3 Drawing Sheets

(56) References Cited

U.S. PATENT DOCUMENTS

| | | | | |
|---|---|---|---|---|
| 11,857,728 | B1 * | 1/2024 | Schultz | A61M 16/0816 |
| 2002/0195104 | A1 * | 12/2002 | Fini | A61M 16/16 128/203.16 |
| 2010/0012127 | A1 * | 1/2010 | Roth | A61M 16/0808 128/205.29 |
| 2010/0089399 | A1 * | 4/2010 | Landis | A61M 16/0427 128/205.12 |
| 2010/0122702 | A1 * | 5/2010 | Reinboth | A61M 16/0808 128/205.27 |
| 2016/0074616 | A1 * | 3/2016 | Grassl | A61M 16/0816 128/202.27 |
| 2018/0221615 | A1 * | 8/2018 | Sevincli | A61M 16/0808 |

* cited by examiner

VENTILATOR CONDENSATION TRAP

CROSS REFERENCE TO RELATED APPLICATIONS

This application is a continuation application of co-pending U.S. application Ser. No. 17/092,287, filed Nov. 8, 2020, now U.S. Pat. No. 11,857,728, which claims the benefit of priority to U.S. Provisional Patent Application No. 62/932,920, filed on Nov. 8, 2019, the disclosures of which are incorporated herein by reference in their entirety.

BACKGROUND

Patients with acute and chronic medical condition can require artificial ventilation through respiratory devices such as an endotracheal tubes or tracheostomy tubes that go into directly into the lungs. During artificial ventilation of a patient, condensation can form on the inner walls of the tubing. This fluid is sometimes called “rain out.” Droplets collect to form pools of liquid inside the tubing. If the tubing containing the pooled fluid is positioned above the patient, the fluid may drain directly into the patient’s airway. Depending on the volume and character of the fluid, this can cause complications, including “drowning,” airway occlusion, asphyxiation, lung damage and infection.

To avoid these complications in a debilitated patient, a caretaker must disconnect ventilation tubing near the patient to pour out fluid formed on the inner walls of the respiratory tubing. This process is labor intensive, messy, frightening, uncomfortable and dangerous. It leads to respiratory arrest during the time interval that the ventilator tubing of the system is disconnected. It is often difficult to get a patient back to their baseline respiratory settings after such a disconnect from the ventilation which may require additional labor-intensive efforts. This process can be very uncomfortable and distressing for the patient as well.

There are systems that reduce humidity to prevent the build-up of condensation, but they involve expensive electrical power technology that can be prohibitively expensive and require a constant power source. There are canisters with caps with an inlet and outlet in the cap that can be placed in the middle of two flexible ventilator tubes so that the flow inlet and flow outlet are positioned adjacent to each other and below the patient to work. This requires extra tubing length which substantially increases dead space. To empty the collection canister that may be on the floor, the system still requires disconnection with all of the undesirable effects. The tubing can still cause the fluid to drain directly into the lungs of a patient if the portion of the tubing between the low-lying collection canister is raised above the level of the endotracheal tube or tracheostomy connector. Because the collection canister is lower than the patient, additional lengths of tubing are required which may adversely affect ventilation or become cumbersome and prone to mishaps.

There are millions of patients that are intubated each year, and most are placed on ventilators. It would be desirable to have a system that allows for removal of rain out without the hazards noted above.

SUMMARY

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Condensation traps are disclosed herein, and generally can comprise a first connector configured to connect directly to a first segment of ventilator tubing, a stem extending distally from the first connector, an internal channel extending through the first connector and the stem, and a reservoir wall surrounding at least a portion of the stem and forming a fluid collection reservoir between an external surface of the stem and an internal surface of the reservoir wall.

Respiratory ventilator systems are also disclosed herein, and can comprise a respiratory ventilator, a patient interface, an expiratory tubing and an inspiratory tubing, each forming a connection between the patient interface and the respiratory ventilator, and any condensation trap disclosed herein connected to the inspiratory tubing or the expiratory tubing in a position such that the first connector is proximal to the patient interface.

Method of removing condensation from mechanical ventilation tubing are also disclosed herein, and can comprise securing a condensation trap within an inspiratory or expiratory segment of ventilator tubing connected to a mechanical ventilator, delivering a humidified gas comprising a water vapor through the inspiratory tubing, allowing a portion of the water vapor to condense within the inspiratory or expiratory segment of ventilator tubing to form water, collecting the water condensed within the within the inspiratory or expiratory segment of ventilator tubing in a ventilator tubing trap, and draining the water from the condensation trap without interrupting ventilation.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DETAILED DESCRIPTION

Figure 1:
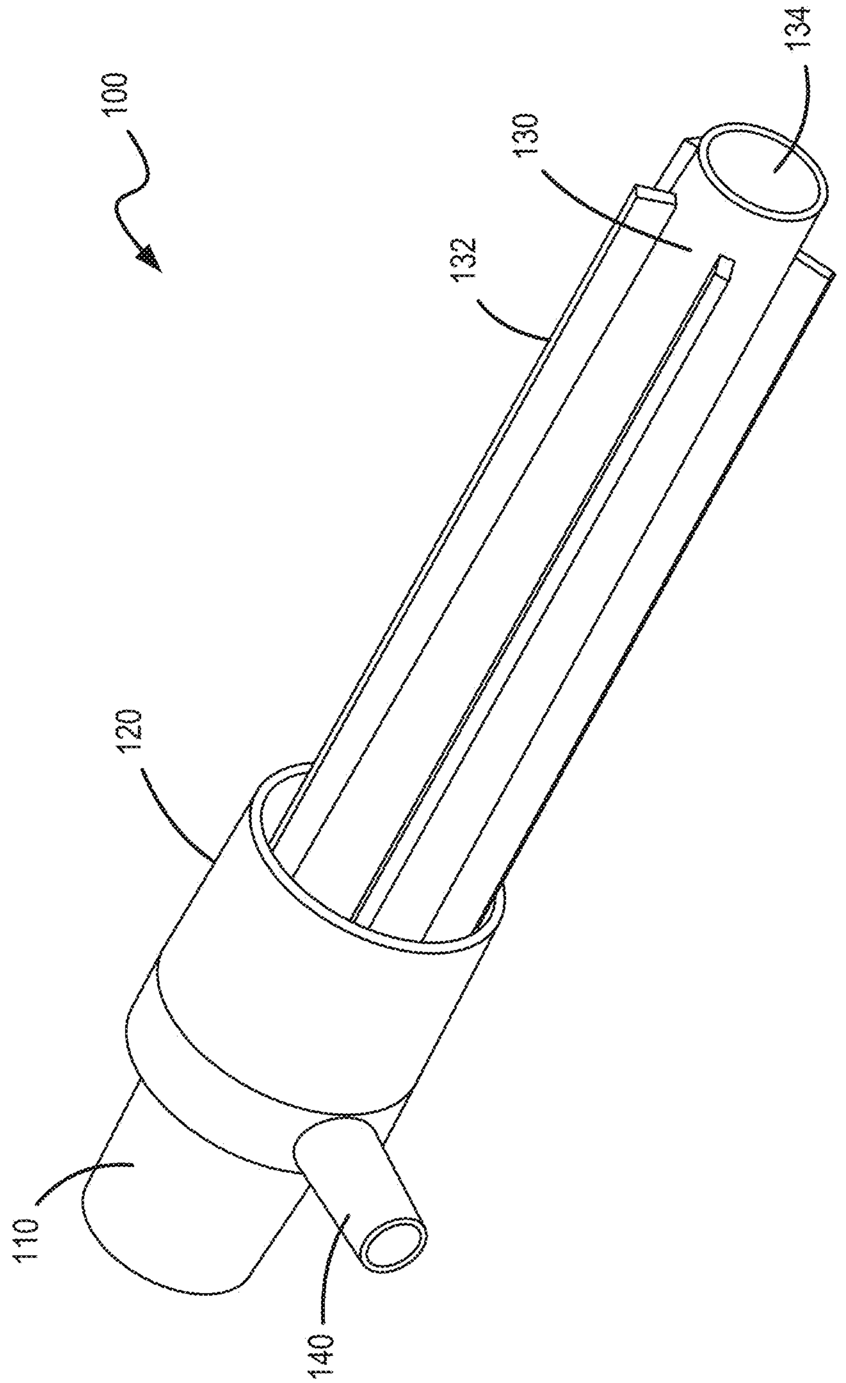
FIG. 1 shows an embodiment of a condensation trap connected within ventilator tubing.

The information that follows describes embodiments with reference to the accompanying figures, in which certain embodiments of the present invention are shown. The foregoing may, however, be embodied in many different forms and should not be construed as limited to the illustrated embodiments set forth herein.

The information that follows details various embodiments of the disclosure. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent aspects of the disclosure that may be taken in isolation and/or combined with other aspects of the disclosure. The skilled person will appreciate that the claimed subject matter extends to such combinations of features and that these have not been recited in detail here in the interest of brevity.

As used herein, components of the devices described herein may be referred to as being proximal or distal. Except where explicitly stated to the contrary, use of proximal herein refers to a component or position in the direction of, or relatively closer to, a patient interface or the patient. In contrast, reference to distal components or positions will be understood to relate to a position or component relatively closer to the ventilator. For instance, where a condensation trap is positioned within an expiratory ventilator tubing, the trap may be connected to a proximal segment of ventilator tubing at a proximal end of the trap, and connected to a distal segment of ventilator tubing at a distal end of the trap. In other aspects, the trap may be connected to a proximal segment of ventilator tubing at a proximal end of the trap, and connected to a distal segment of ventilator tubing also at a proximal end of the trap. Embodiments are presented and described below which illustrate this usage.

Devices, systems, and methods are disclosed herein that represent improvements regarding issues of rain out during ventilation as discussed above. Generally, condensation traps are described herein for the purpose of collecting condensation within a ventilator tubing, and preventing the condensation from entering an airway of the patient. Condensation traps contemplated herein generally can be applied within a mechanical respiratory ventilator, and ventilator systems are also contemplated herein. In certain aspects, respiratory ventilator systems can comprise a mechanical ventilator, a patient interface, an inspiratory tubing providing air flow from the ventilator to the patient interface, an expiratory tubing providing air flow from the patient interface to the mechanical ventilator, and a condensation trap.

In conventional ventilator systems, the position of condensation traps can be limited to positions within the tubing or at the ventilator relatively far away from the patient interface, such that some amount of dead space within the tubing between the trap and the patient remains. Certain aspects disclosed herein can reduce or eliminate the dead space within the ventilator tubing according the placement of the condensation trap. In certain aspects, the condensation trap can be positioned directly adjacent the patient interface, within 3 inches of the patient interface, within 6 inches of the patient interface, within 12 inches of the patient interface, or within 18 inches of the patient interface. In certain aspects, the condensation trap can be connected directly to the patient interface. Additionally, or alternatively, the condensation trap can be positioned above the patient or patient interface without interfering with other equipment and operation of the condensation trap. In certain aspects, the condensation trap can be connected in-line with the tubing at any position described above, such that the trap does not present additional cumbersome equipment adjacent the patient and patient interface.

Condensation traps disclosed herein can be connected within an inspiratory tubing line, within an expiratory tubing line, or both. Alternatively, the condensation trap may be formed proximal to a juncture of the inspiratory and expiratory lines, such that each line is serviced by the trap. In such aspects, the condensation trap can be within the patient interface, as a removable and separate piece, or alternatively as an integral molded component of the patient interface. Other arrangements which reduce the dead space where condensation may accumulate without being subject to removal from the tubing are also contemplated herein. In certain aspects, the amount of dead space between the patient interface and the condensation trap can be less than 500 ml, less than 250 ml, less than 100 ml, less than 50 ml, or less than 20 ml.

The patient interface is not limited to any particular shape or construction, and generally can be any that provide a junction for inspiratory and expiratory tubing and the patient's airways, such as can allow for ventilation of a patient. In certain aspects, the patient interface can comprise a plastic mask, e.g., a half face mask, full face mask, or complete enclosure. In such aspects, the patient interface can connect directly to a condensation trap described herein at a proximal end of the trap. In certain aspects, the patient interface can comprise an endotracheal tube connector or tracheostomy adapter. Other patient interfaces are contemplated within this disclosure as would be understood by a person of ordinary skill in the art.

Further aspects of the ventilator systems disclosed herein can comprise a humidifier positioned at any place in the system. In certain aspects, the air entering the patient via the inspiratory line can be humidified to improve patient comfort. In such aspects, a humidifier can be present within the inspiratory line, or within the ventilator. In certain aspects disclosed herein, an inspiratory humidity of at least 20%, at least 30%, at least 50%, at least 70%, or at least 90% can be maintained without risk of rain out in a dead space within the either the inspiratory or expiratory line.

Condensation traps disclosed herein generally can comprise a first connector configured to connect to a proximal segment of ventilator tubing or directly to a patient interface. The trap can further comprise a stem extending distally within the trap. In certain aspects, the stem can extend from the first connector toward a distal end of the trap. The stem can comprise an internal channel to allow passage of humidified air into and through the trap, either from the patient or a humidifier. Thus, in certain aspects, the stem can be a hollow cylindrical component that extends from the first connector at a proximal region into a distal portion of the tubing.

Referring to FIG. 1, an embodiment of the condensation trap 100 is shown comprising a first connector 110, a reservoir wall 120, stem 130, and drain 140 connected to a fluid reservoir formed between the internal surface of the reservoir wall and the external surface of the stem. Also shown are spacing elements 132 as ridges radially extending from the stem, and substantially along the length of the stem. In certain aspects, these spacing elements can extend to the end of the stem, or beyond the stem, and generally take any form suitable to prevent the distal end of the stem from resting on the interior surface of the ventilator tubing. Spacing elements also can comprise a shape or texture advantageous to the condensation of water, such as would promote condensation of water vapor and direct the condensed water into the fluid reservoir to be drained. Certain aspects can comprise a plurality of spacing elements, and can be in a range from 3 to 12 spacers, from 4 to 8 spacers, or from 4 to 6 spacers. The surface of spacers can be any suitable for the condensation trap, and in certain aspects may be configured to aid condensation. In certain aspects, surface are of the spacers can be augmented by addition of a rough or textured surface to any or all of the spacing elements. In such aspects, the condensation of water vapor may occur preferentially within the ventilator trap, relative to other areas within the tubing.

Figure 2:
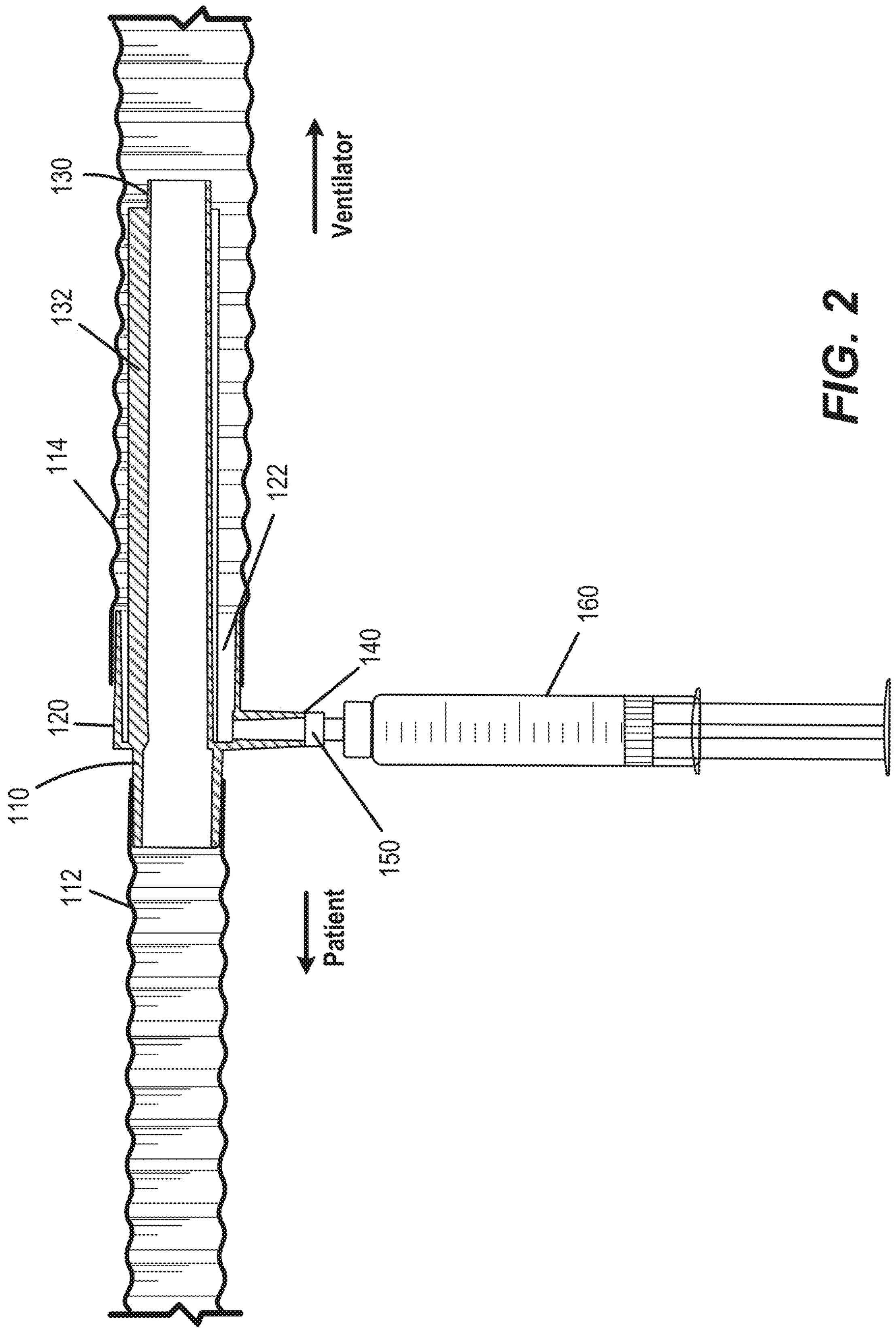
FIG. 2 shows the embodiment of FIG. 1, wherein a plunger syringe is connected to the drain via a drain valve for removing fluid from the trap.

FIG. 2 provides the embodiment of FIG. 1 connected to a proximal segment 112 at first connector 110 and a distal tubing segment 114 at the reservoir wall 120. As is shown, the reservoir wall serves as a second connector to ventilator tubing such as allows the condensation trap 100 to be inserted within the tubing line. Fluid reservoir 122 is formed by the connection between reservoir wall 120 and stem 130. Drain 140 is shown as being terminated by closure 150 and connected to syringe 160 for removal of fluid within the fluid reservoir.

Generally, the volume of the fluid reservoir in condensation traps disclosed herein is not limited to any particular volume, and can be any that allows continuous ventilation. Thus, in certain aspects, the fluid reservoir can have a volume of at least 5 ml, at least 10 ml, at least 20 ml, at least 50 ml, or at least 100 ml. In other aspects, the fluid reservoir can have a volume in a range from about 10 ml to 1 L, from about 50 ml to about 500 ml, or from about 50 ml to about 250 ml. In these aspects, the drain can be accessed by any mechanism or device configured to remove fluid from the fluid reservoir. For instance, closure 150 can be a needleless valve which opens upon insertion of a Luer connection into the closure. Such closures are described in detail within U.S. Pat. No. 7,713,247. Additional closures allowing straightforward connection between a syringe or other fluid withdrawal device and the fluid within the fluid reservoir are also contemplated within this disclosure.

In certain aspects, the reservoir wall can share a dimension with the first connector. For instance, the first connector and reservoir wall can have substantially similar external diameter.

Advantageously, the drain configured in this manner can allow the fluid in the fluid reservoir to be removed without interrupting ventilation. Particularly, systems and traps as disclosed above allow for the rain-out condensation to be removed intermittently without disconnecting the condensation trap from the ventilator tubing, without disconnecting the patient from the patient interface, and without interrupting airflow delivered to the patient. Moreover, fluid removal can be achieved without risk of aspirating the condensed fluid into the patient's airways by agitating equipment to disconnect as described.

Figure 3:
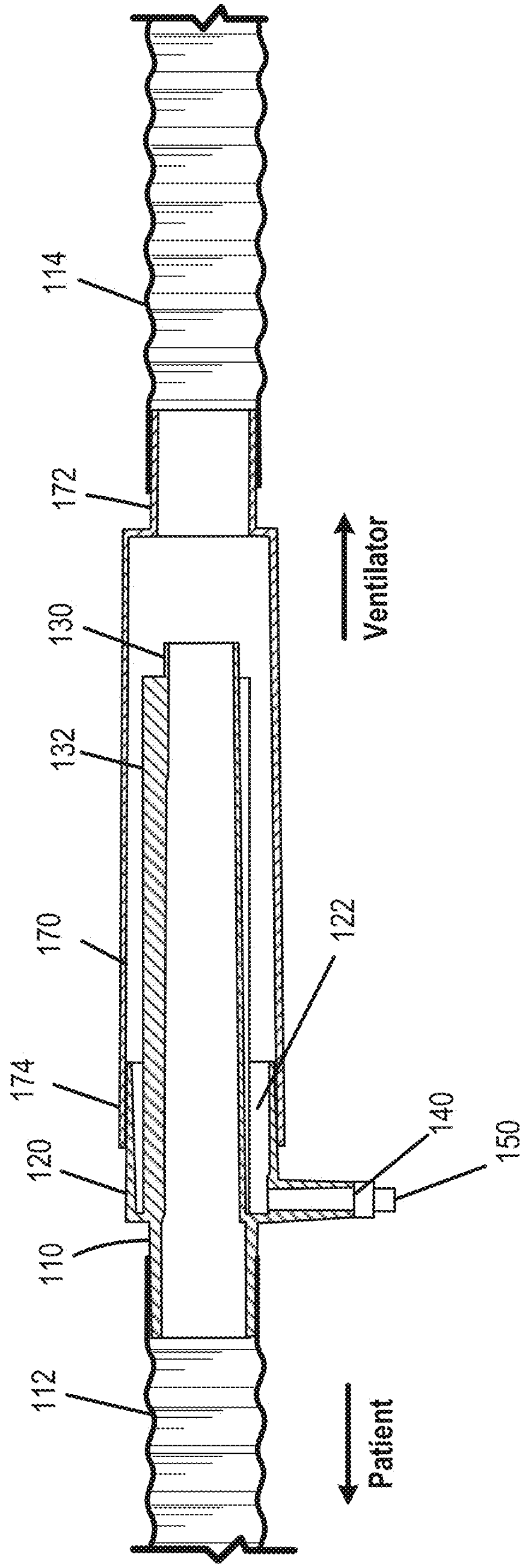
FIG. 3 shows an embodiment of a condensation trap within a capsule.

FIG. 3 shows an alternate configuration of the condensation trap comprising a rigid capsule encompassing the stem. In contrast to the embodiment of FIGS. 1-2, the distal segment of ventilator tubing is not connected to the reservoir wall, but a second ventilator tubing connector provided at the distal portion of the capsule condensation trap. As shown, distal segment 114 is connected to a capsule 170 by a second connector 172 at a position proximal the distal end of stem 130. Such aspects have advantages as providing a connection within a ventilator tubing of equal diameter, and also providing a fixed construction surrounding the stem, such as may provide greater assurance that the interior surface of the distal tubing segment 114 does not contact the exterior surface of stem 130 during operation. Capsule 170 is also connected to reservoir wall 120 at proximal end 174 of the capsule 170 to complete the ventilatory circuit.

In aspects comprising a capsule, the capsule can be any shape or size suitable for connecting the reservoir wall. In certain aspects, the capsule can be fixed to the reservoir wall, or alternatively, removable from the reservoir wall. In certain aspects, the trap can be entirely monolithic. Thus, the capsule may be formed as a unitary piece with the reservoir wall. In such aspects, the volume of the fluid collection reservoir may be defined by the length of the stem.

In certain aspects, the fluid collection reservoir (e.g., sump) may have a drain as depicted by element 140 in FIGS. 1-3. In certain aspects, the drain may be smaller than the inner diameter of the stem. The drain may have a closure, the closure comprising an adapter to allow engagement with a syringe or other suction device for draining off liquid. In certain aspects, the closure may be a Luer adapter. In other aspects, the drain can comprise a valve which permits opening and closing of the valve from negative pressure removal or gravity drainage without disconnecting the ventilatory circuit and therefore maintaining the pressure, volume and flow of gas within the ventilatory circuit without the significant interruption associated with prior art techniques.

Systems disclosed herein can comprise a plurality of "respiratory" connectors, including at least one proximal connector and at least one distal connector. In certain aspects, such as shown in FIG. 1, the first and second connectors can each be respiratory connectors as defined herein. In other aspects, the reservoir wall also can be a respiratory connector. Respiratory connectors can be any ISO standard respiratory connector. Certain aspects can comprise multiple respirator connectors and multiple respirator connectors of different sizes and the connectors may be monolithic with each other, removable or interchangeable.

The stem or central channel may have a distal end that extends distal to the endotracheal tube adapter opening, and may have an inner diameter larger than the inner diameter of a tracheostomy tube or endotracheal tube. The stem and at least one of the respiratory connectors may be in a coaxial relationship. The stem may extend within the ventilator tubing in a coaxial relationship. The invention may than trap fluid on the gravity dependent portions of the tubing from flowing into the stem and into the lungs, by instead collecting around the stem. The fluid could then be drained off the sump without disrupting the ventilation process and avoid the disadvantages of the prior art. The fluid may be drained off the sump by intermittently applying a small amount of negative pressure with a device such as a syringe or intermittent vacuum. The fluid may be removed from sump by intermittently opening a closure and allowing the positive pressure of the system to push the fluid out. In this sense, it will be understood by those of skill in the art that aspects of the present invention can provide a small, portable, inexpensive, mechanical safety device that does not substantially increase dead space and can be positioned above the level of an endotracheal tube or tracheostomy adapter inlet. The invention could provide a simple inexpensive device that could reduce the risks of "backwash" of rainout that may lead to infection, ventilator associated pneumonias, lung damage, patient distress, patient morbidity and patient mortality.

Methods of preventing rainout and removing condensation from mechanical ventilation tubing are also disclosed herein. In certain aspects, methods can comprise securing a condensation trap as disclosed herein within an inspiratory or expiratory segment of ventilator tubing in a mechanical ventilator, delivering a gas comprising a water vapor to a subject with the mechanical ventilator, allowing a portion of the water vapor to condense within the inspiratory or expiratory segment of ventilator tubing to form water, collecting the water within the ventilator tubing trap, and draining the water from the ventilator tubing trap.

Methods disclosed may comprise these operations conducted in any order appropriate, and generally within the principles applicable to condensation traps and systems discussed above. For example, collecting the water within the trap can comprise collecting at least 5 ml, at least 10 ml, at least 20 ml, at least 50 ml, or at least 100 ml of the fluid within a fluid reservoir, or any other range disclosed herein. Other aspects of the methods will be apparent to those of skill in the art according to details provided in individual aspects below and relevant to the condensation traps and systems described above.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect. A ventilator condensation trap comprising:

a first connector;

a stem extending distally from the first connector;

an internal channel extending from the first connector through the stem; and a reservoir wall surrounding at least a portion of the stem to form a fluid collection space between an external surface of the stem and an internal surface of the reservoir wall.

Aspect. The condensation trap of the preceding aspect, further comprising a drain is in fluid connection with the fluid collection space.

Aspect. The condensation trap of the preceding aspect, wherein the first connector and the second connector are each an ISO 5356-1 compliant respiratory connector.

Aspect. The condensation trap of the preceding aspect, further comprising a capsule connected to the second connector, the capsule comprising a capsule connector and a distal segment of ventilator tubing.

Aspect. The condensation trap of any one of the preceding aspects, wherein the first, second, and capsule respiratory connectors are each independently any suitable connector disclosed herein, including ISO 5356-1 compliant respiratory connectors.

Aspect. The condensation trap of any one of the preceding aspects, wherein the drain comprises a connector that is an ISO complaint 80369-7 connector.

Aspect. The condensation trap of any one of the preceding aspects, wherein the drain comprises a connector that is not an ISO complaint 80369-7 connector.

Aspect. The condensation trap of any one of the preceding aspects, wherein the first connector is smaller than the second connector.

Aspect. The condensation trap of any one of the preceding aspects, wherein the first, second, and capsule connectors each comprise any suitable shape disclosed herein, e.g., cylindrical, conical, non-circular, angled, elongated.

Aspect. The condensation trap of any one of the preceding aspects, wherein the first connection is tapered toward the proximal end of the condensation trap, and the second connection is tapered toward the distal end of the condensation trap.

Aspect. The condensation trap of any one of the preceding aspects, wherein the first, second, and capsule connectors each independently have any length disclosed herein Aspect. The condensation trap of any one of the preceding aspects, wherein any of the first, second, and capsule connectors are coaxial with each other.

Aspect. The condensation trap of any one of the preceding aspects, wherein the respiratory connectors consist of ISO 5356 compliant respiratory connectors.

Aspect. The condensation trap of any one of the preceding aspects, wherein the respiratory connectors comprise ISO 5356 compliant respiratory connectors for use in neonatal and paediatric breathing systems.

Aspect. The condensation trap of any one of the preceding aspects, wherein the respiratory connectors consist of ISO 5356 compliant respiratory connectors for use in neonatal and paediatric breathing systems.

Aspect. The condensation trap of any one of the preceding aspects, wherein the respiratory connectors comprise ISO 5356 compliant respiratory connectors for general use in breathing systems.

Aspect. The condensation trap of any one of the preceding aspects, wherein the respiratory connectors consist of ISO 5356 compliant respiratory connectors for general use in breathing systems.

Aspect. The condensation trap of any one of the preceding aspects, wherein the respiratory connectors comprise ISO 5356 compliant respiratory connectors intended for vaporizers, but not for use in breathing systems.

Aspect. The condensation trap of any one of the preceding aspects, wherein the respiratory connectors consist of ISO 5356 compliant respiratory connectors intended for vaporizers, but not for use in breathing systems.

Aspect. The condensation trap of any one of the preceding aspects, wherein the respiratory connectors comprise ISO 5356 compliant respiratory connectors intended for connection of a breathing system to an anaesthetic gas scavenging system.

Aspect. The condensation trap of any one of the preceding aspects, wherein the respiratory connectors consist of ISO 5356 compliant respiratory connectors intended for connection of a breathing system to an anaesthetic gas scavenging system.

Aspect. The condensation trap of any one of the preceding aspects, wherein the respiratory connectors comprise a combination of ISO 5356 compliant respiratory connectors.

Aspect. The condensation trap of any one of the preceding aspects, wherein the respiratory connectors consist of a combination of ISO 5356 compliant respiratory connectors.

Aspect. The condensation trap of any one of the preceding aspects, wherein the stem is any shape disclosed herein, e.g., cylindrical, elongated, etc.

Aspect. The condensation trap of any one of the preceding aspects, wherein the stem extends distal to a distal end of the second connector.

Aspect. The condensation trap of any one of the preceding aspects, further comprising a spacer extending radially from the stem.

Aspect. The condensation trap of any one of the preceding aspects, wherein the spacer comprises a spacing ridge (or a plurality of spacing ridges, e.g., 2, 3, 6, 10, etc.) along its external surface.

Aspect. The condensation trap of any one of the preceding aspects, wherein the spacing ridge extends to the distal end of the stem, or within any distance of the distal end of the stem disclosed herein, e.g., ½", 1", 2", etc.

Aspect. The condensation trap of any one of the preceding aspects, wherein the spacer extends to the opening of stem.

Aspect. The condensation trap of any one of the preceding aspects, wherein the spacer extends beyond the opening of the stem.

Aspect. The condensation trap of any one of the preceding aspects, wherein the stem extends beyond the spacer.

Aspect. The condensation trap of any one of the preceding aspects, wherein the spacer has a radial width less than one of the connectors.

Aspect. The condensation trap of any one of the preceding aspects, wherein the spacer has a radial width less than one of the respiratory connectors.

Aspect. The condensation trap of any one of the preceding aspects, wherein the stem extends beyond the respiratory connector on the ventilator end.

Aspect. The condensation trap of any one of the preceding aspects, wherein the stem extends within the respiratory connector.

Aspect. The condensation trap of any one of the preceding aspects, wherein the stem channel extends between a first and second ISO compliant respiratory connector.

Aspect. The condensation trap of any one of the preceding aspects, wherein the spacer is configured to assist positioning of the internal channel of the stem away from an internal wall of a ventilation tube conduit to prevent fluid from entering the internal channel when a portion of the ventilation tube surrounding the stem and the stem are non-parallel.

Aspect. The condensation trap of any one of the preceding aspects, wherein the spacing ridge extends proximally within the fluid collection space.

Aspect. The condensation trap of any one of the preceding aspects, wherein the spacing ridge comprises a proximal gap adjacent the proximal surface of the fluid collecting space to allow fluid to proceed toward the drain.

Aspect. The condensation trap of any one of the preceding aspects, wherein the spacer comprises a circumferential gap adjacent the proximal surface of the fluid collecting space.

Aspect. The condensation trap of any one of the preceding aspects, wherein the spacing ridge is arranged in a spiral or longitudinal formation around the stem.

Aspect. The condensation trap of any one of the preceding aspects, wherein the devices comprises a surface for increasing condensation such as ridges.

Aspect. The condensation trap of any one of the preceding aspects, wherein the spacing ridge comprises any condensing material disclosed herein, e.g., metals.

Aspect. The condensation trap of any one of the preceding aspects, wherein the condensing material is different from that of the interior surface of the internal channel and/or the material of the ventilator tubing.

Aspect. The condensation trap of any one of the preceding aspects, wherein the fluid collection space has a volume in any range disclosed herein, e.g., from about 1 ml to about 10 ml, greater than 3 ml, greater than 5 ml but less than 10 ml, greater than 5 ml but less than 30 ml, greater than 5 ml but less than 60 ml, so that the fluid can be drained off by a standard plunger syringe.

Aspect. The condensation trap of any one of the preceding aspects, wherein the internal channel is cylindrical and has an inner diameter greater than a standard ISO 5356 respiratory connector.

Aspect. The condensation trap of any one of the preceding aspects, wherein the internal channel has an inner cross-sectional area larger than that of an endotracheal tube.

Aspect. The condensation trap of any one of the preceding aspects, wherein the height of the fluid collection space is greater than that of a typical endotracheal tube adapter.

Aspect. The condensation trap of any one of the preceding aspects, wherein the drain comprises any suitable drain connector disclosed herein, e.g., a cap, a syringe membrane, needle membrane, valve, or stopcock valve.

Aspect. The condensation trap of any one of the preceding aspects, wherein the drain comprises a Luer adapter.

Aspect. The condensation trap of any one of the preceding aspects, wherein the drain comprises a valve positioned adjacent the fluid collection space.

Aspect. The condensation trap of any one of the preceding aspects, wherein the stem comprises an outer wall that is spaced from the inner wall of a capsule or ventilation tubing.

Aspect. The condensation trap of any one of the preceding aspects wherein the stem comprises an outer wall that is circumferentially spaced from the inner wall of a capsule or ventilation tubing.

Aspect. The condensation trap of any one of the preceding aspects, wherein the stem comprises a plurality of spacing ridge with gaps between ridges and the inner wall of a capsule or ventilation tubing.

Aspect. The condensation trap of any one of the preceding aspects, wherein the respiratory connectors comprise ISO 5356 compliant respiratory connectors.

Aspect. The condensation trap of any one of the preceding aspects, wherein the respiratory connectors consist of ISO 5356 compliant respiratory connectors.

Aspect. The condensation trap of any one of the preceding aspects, wherein the respiratory connectors do not consist of ISO 5356 compliant respiratory connectors.

Aspect. The condensation trap of any one of the preceding aspects, further comprising multiple drains connected with the fluid collection reservoir.

Aspect. The condensation trap of any one of the preceding aspects, wherein the drain comprises an ISO complaint 80369-7 connector.

Aspect. The condensation trap of any one of the preceding aspects, wherein the drain does not comprise an ISO complaint 80369-7 connector.

Aspect. The condensation trap of any one of the preceding aspects, wherein the drain comprises a valve, plug, cap, stopcock, check valve, pierceable membrane, clamp, clamped tubing, a fitting compatible with a luer lock syringe, a fitting compatible with a catheter tip syringe or any combination of these elements.

Aspect. A respiratory ventilator comprising the ventilator tubing trap of any of the preceding aspects.

Aspect. The respiratory ventilator of the preceding aspect, wherein the ventilator tubing trap is connected to a proximal segment of an expiratory tubing by the first connector and a distal segment of the expiratory tubing by the second connector.

Aspect. The respiratory ventilator of any one of the preceding aspects, wherein the ventilator tubing trap is connected to a proximal segment of an expiratory tubing by the first connector and a distal segment of the expiratory tubing by the capsule connector.

Aspect. The respiratory ventilator of any one of the previous aspects, further comprising a humidifier.

Aspect. A method of removing condensation from mechanical ventilation tubing, the method comprising:

securing a condensation trap of any of the preceding aspects within an inspiratory or expiratory segment of ventilator tubing in a mechanical ventilator;

delivering a gas comprising a water vapor to a subject with the mechanical ventilator;

allowing a portion of the water vapor to condense within the inspiratory or expiratory segment of ventilator tubing to form water;

collecting the water within the ventilator tubing trap; and draining the water from the ventilator tubing trap.

Aspect. A method of removing condensation from mechanical ventilation tubing, the method comprising:

securing an inline condensation trap of any of the preceding aspects inline within an inspiratory or expiratory segment of ventilator tubing in a mechanical ventilator;

delivering a gas comprising a water vapor to a subject with the mechanical ventilator;

allowing a portion of the water vapor to condense within the inspiratory or expiratory segment of ventilator tubing to form water;

collecting the water within the ventilator tubing trap; and draining the water from the ventilator tubing trap without interrupting the ventilation process.

Aspect. A method of removing condensation from mechanical ventilation tubing, the method comprising:

securing a condensation trap of any of the preceding aspects within an inspiratory or expiratory segment of ventilator tubing in a mechanical ventilator;

delivering a gas comprising a water vapor to a subject with the mechanical ventilator;

allowing a portion of the water vapor to condense within the inspiratory or expiratory segment of ventilator tubing to form water;

collecting the water within the ventilator tubing trap; and draining the water from the ventilator tubing trap without interrupting the ventilation process.

Aspect. A method of removing condensation from mechanical ventilation tubing, the method comprising:

securing an access port within an inspiratory or expiratory segment of ventilator tubing in a mechanical ventilator;

delivering a gas comprising a water vapor to a subject with the mechanical ventilator;

allowing a portion of the water vapor to condense within the inspiratory or expiratory segment of ventilator tubing to form water;

collecting the water within the ventilator tubing trap; and using a closed vacuum system to drain the water from the ventilator tubing without disrupting the positive pressure ventilation process.

Aspect. The method of the preceding aspect, wherein the condensation trap is secured at a position near the patient, e.g., less than about 3" or in a range from about 1" to about 12".

Aspect. The method of any one of the preceding aspects, wherein the condensation trap is secured above the patient.

Aspect. The method of any one of the preceding aspects, wherein the condensation trap is positioned above the level of an endotracheal tube adapter or tracheostomy adapter.

Aspect. The method of any one of the preceding aspects, wherein the draining step comprises coupling a syringe to a drain, and withdrawing the liquid collected in the trap.

Aspect. The method of any one of the preceding aspects, wherein the draining step comprises engaging a valve to maintain the pressure within the ventilation tubing during the draining step.

Aspect. The method of any one of the preceding aspects, wherein delivering the humidified gas can be conducted simultaneously with the draining step.

Aspect. The method of any one of the preceding aspects, wherein the pressure within the mechanical ventilator settings are maintained within the same range before, during and after draining the fluid.

Aspect. The method of any one of the preceding aspects, wherein an alarm notifies a caregiver when there is sufficient buildup of fluid.

Aspect. The method of any one of the preceding aspects, wherein fluid is automatically removed from the trap.

Aspect. A method of using a condensation sump in line with mechanical ventilation tubing to prevent death. Aspect. The method of any one of the preceding aspects, wherein at least 50% (or at least 80%, or at least 95%, or any other suitable range disclosed herein) of the water condensed in the distal portion of the expiratory tubing segment is collected within the condensation trap.

Aspect. The method of any one of the preceding aspects, wherein less than 10% (or less than 5%, or less than 1%, or any other suitable range disclosed herein) of the water condensed in the distal portion of the expiratory tubing segment falls into the lungs.

Aspect. The method of any one of the proceeding aspects, wherein rainout within the proximal segment of the expiratory tubing is reduced by at least about 50%, or any other suitable range disclosed herein.

Aspect. A condensation drain for a mechanical ventilation inspiratory or expiratory tubing system where the drain comprises, a luer connector, a female luer connector, a male luer connector, a luer lock connector, an occluder, a cap, a valve, membrane, stopper or a pathway that can be opened or pierced without losing pressure in ventilation system.

Aspect. A condensation drain for a mechanical ventilation inspiratory or expiratory tubing system where the drain is coaxial with connector, is not coaxial with connector, is perpendicular with respiratory connector, does not extend from stem, does not extend from ET adapter or tracheostomy tube adapter or extends from a wall between ventilator adapter (e.g. for an endotracheal tube or tracheostomy) and ventilator.

The invention claimed is:

1. A ventilator condensation trap comprising:

a first connector configured to connect directly to a first segment of ventilator tubing;

a stem extending distally from the first connector;

an internal channel extending through the first connector and the stem;

a reservoir wall surrounding at least a portion of the stem and forming a fluid reservoir between an external surface of the stem and an internal surface of the reservoir wall; and a drain connected with the fluid reservoir, wherein the drain is a needleless access valve in a closed position.

2. The ventilator condensation trap of claim 1, wherein an external surface of the reservoir wall comprises a second connector configured to connect directly to a second segment of ventilator tubing.

3. The ventilator condensation trap of claim 2, wherein the first and second segments of ventilator tubing have a substantially similar diameter.

4. The ventilator condensation trap of claim 1, further comprising a capsule connected to the reservoir wall at a proximal end of the capsule, the capsule comprising a second connector at a distal end of the capsule configured to connect directly to a second segment of ventilator tubing.

5. The ventilator condensation trap of claim 4, wherein the first connector, reservoir wall, or any combination thereof, is an ISO 5356 compliant respiratory connector.

6. The ventilator condensation trap of claim 1, wherein the stem extends beyond a distal end of the reservoir wall.

7. The ventilator condensation trap of claim 1, wherein the stem comprises a plurality of spacing ridges extending radially from the external surface of the stem.

8. The ventilator condensation trap of claim 7, wherein the plurality of spacing ridges comprises from 3 to 12 spacing ridges.

9. The ventilator condensation trap of claim 7, wherein each of the plurality of spacing ridges extends radially from the stem a distance in a range from 5 mm to 25 mm.

10. The ventilator condensation trap of claim 7, wherein the plurality of spacing ridges comprises a textured surface configured to increase condensation.

11. The ventilator condensation trap of claim 1, wherein the fluid reservoir has a volume in a range from 5 ml to 60 ml.

12. A method of removing condensation from mechanical ventilation tubing, the method comprising:
- securing the ventilator condensation trap of claim 1 within an inspiratory or an expiratory segment of ventilator tubing connected to a mechanical ventilator;
- delivering a humidified gas comprising a water vapor through the inspiratory segment;
- allowing a portion of the water vapor to condense within the inspiratory or the expiratory segment of ventilator tubing to form water;
- collecting the water condensed within the inspiratory or the expiratory segment of ventilator tubing in the ventilator condensation trap; and
- draining the water from the ventilator condensation trap without interrupting ventilation.

13. The method of claim 12, wherein the ventilator condensation trap is secured above a patient.

14. The method of claim 12, wherein draining the water from the ventilator condensation trap is performed automatically.

15. The method of claim 12, wherein at least 50% of the water condensed in a portion of the expiratory segment distal to a patient is collected within the ventilator condensation trap.

16. A respiratory ventilator system comprising:
- a respiratory ventilator;
- a patient interface;
- an expiratory tubing and an inspiratory tubing, each forming a connection between the patient interface and the respiratory ventilator;
- a ventilator condensation trap comprising:
  - a first connector configured to connect directly to a first segment of ventilator tubing;
  - a stem extending distally from the first connector;
  - an internal channel extending through the first connector and the stem; and
  - a reservoir wall surrounding at least a portion of the stem and forming a fluid reservoir between an external surface of the stem and an internal surface of the reservoir wall;
- wherein the ventilator condensation trap is connected to the inspiratory tubing or the expiratory tubing in a position such that the first connector is proximal to the patient interface; and
- wherein the ventilator condensation trap is positioned such that the first connector is within 12" of the patient interface.

17. The respiratory ventilator system of claim 16, further comprising a humidifier.

18. The respiratory ventilator system of claim 16, wherein the ventilator condensation trap is connected to the inspiratory tubing.

* * * * *